(12) United States Patent
Camedda et al.

(10) Patent No.: US 8,070,803 B2
(45) Date of Patent: Dec. 6, 2011

(54) UNIVERSAL ANNULOPLASTY SYSTEM

(75) Inventors: Caroline Camedda, Saint Cloud (FR); Kevin Le Gallo, Paris (FR)

(73) Assignee: Peters Surgical, Bobigny (FR)

( * ) Notice: Subject to any disclaimer, the term of this patent is extended or adjusted under 35 U.S.C. 154(b) by 783 days.

(21) Appl. No.: 12/034,285

(22) Filed: Feb. 20, 2008

(65) Prior Publication Data

US 2009/0210051 A1 Aug. 20, 2009

(51) Int. Cl.
*A61F 2/24* (2006.01)
(52) U.S. Cl. .................. 623/2.36; 606/146; 606/148
(58) Field of Classification Search .............. 623/2.1, 623/2.11, 2.36; 124/42, 86; 606/146, 148
See application file for complete search history.

(56) References Cited

U.S. PATENT DOCUMENTS

| | | | | |
|---|---|---|---|---|
| D302,358 S | * | 7/1989 | Rezmer | D22/107 |
| 4,898,155 A | * | 2/1990 | Ovil et al. | 606/144 |
| 5,011,028 A | * | 4/1991 | Sweeney | 211/60.1 |
| 5,019,032 A | * | 5/1991 | Robertson | 600/29 |
| 5,961,539 A | | 10/1999 | Northrup, III et al. | |

OTHER PUBLICATIONS

Carpentier et al., *A new reconstructive operation for correction of mitral and tricuspid insufficiency*, The Journal of Thoracic and Cardiovascular Surgery, vol. 61, No. 1, Jan. 1971, pp. 1-13.
Carpentier et al., *The "Physio-Ring": An Advanced Concept in Mitral Valve Annuloplasty*, The Society of Thoracic Surgeons, Jan. 30-Feb. 2, 1995, pp. 1177-1186.
Duran et al., *Clinical and Hemodynamic Performance of a Totally Flexible Prosthetic Ring for Atrioventricular Valve Reconstruction*, Departments of Cardiovascular Surgery and Radiology, Jan. 26-28, 1976, pp. 458-463.
Cosgrove et al., *Initial Experience With the Cosgrove-Edwards Annuloplasty System*, The Society of Thoracic Surgeons, Jan. 30-Feb. 1, 1995, pp. 499-504.

* cited by examiner

*Primary Examiner* — Darwin Erezo
*Assistant Examiner* — Gregory Anderson
(74) *Attorney, Agent, or Firm* — Pauley Petersen & Erickson (57) ABSTRACT

A holder for an annuloplasty ring is disclosed. It comprises a plurality of linked-together suture platforms, wherein said holder comprises an upper face, a lower face, and a closed peripheral edge with means for accommodating and supporting said suture platforms of said annuloplasty ring.

17 Claims, 13 Drawing Sheets

UNIVERSAL ANNULOPLASTY SYSTEM

BACKGROUND OF THE INVENTION

The invention relates generally to a holder for an annuloplasty ring which consists in a plurality of linked-together suture platforms.

Modern ring annuloplasty techniques originate from Carpentier's original concept of "valvular remodeling on a frame" published in French in 1969 and in English in 1971 (Carpentier A, et al, A new reconstructive operation for correction of mitral and tricuspid insufficiency. J Thorac Cardiovasc Surg 1971; 61:1-13). His idea was to permanently correct the valvular insufficiency by resizing and reshaping the dilated annulus with a preformed rigid ("non-deformable") ring affixed to the annulus with numerous interrupted horizontal mattress sutures.

In the interest of preserving the flexibility of the mitral annulus, Duran and Ubago (Duran C G, Ubago J L, Clinical and hemodynamic performance of a totally flexible prosthetic ring for atrioventricular valve reconstruction. Ann Thorac Surg 1976; 22:458-463) introduced a completely circumferential flexible ring in 1976. In 1995, Cosgrove et al (Cosgrove D M III, et al, Initial experience with the Cosgrove-Edwards annuloplasty system. Ann Thorac Surg 1995; 60:499-504) introduced a partially circumferential flexible band attached only to the posterior mitral leaflet of the annulus. In the same year, Carpentier et al. (Carpentier, A F, et al. The "Physio-Ring": An advanced concept in mitral valve annuloplasty. Ann Thorac Surg 1995; 60:1177-1186) introduced the "Physio-Ring," i.e. a complete ring with a "combination of selective rigidity at the anterior section and selective flexibility at the posterior section.

The short- and long-term results of mitral repair are impressive. It appears to be the only heart valve operation which has the potential to return patients to expected survival at least for 10 years, and possibly longer, if performed before significant left ventricular dysfunction and symptoms. It has a lower operative mortality rate and better long-term survival than replacement and has long-term re-operation rates comparable to those of mechanical valve replacement, and much better than tissue valve replacement. The durability of repair is impressive as evidenced by the very low long-term re-operation rates in Carpentier's original series.

It is quite possible that an annuloplasty ring with overall flexibility and segmental rigidity, which preserves the normal three-dimensional shape of the annulus, prevents crimping upon implantation, maximizes apposition of the ring to the tissue annulus with each individual suture, minimizes shared tensions between individual sutures and (in the case of the mitral annulus) fully engages the intertrigonal fibrous skeleton, will qualify as a "next generation" ring.

In 1998, Northrup and al introduced the concept of a suture-platform, which forms the basis of the "Northrup Universal Annuloplasty System". When the suture-platforms were placed in series and covered with a flexible material, a unique annuloplasty concept with segmental rigidity and overall flexibility was achieved.

In the case of the suture-platform, foreshortening or crimping of the overlying flexible ring material is impossible because each mattress suture engages an individual rigid suture-platform within the mattress suture loop.

In U.S. Pat. No. 5,961,539 is disclosed an annuloplasty ring which consists in a plurality of discrete segments which remain isolated from each other, even after having been sutured. Each segment rests on an individual holder.

This ring is suitable for the annuloplasty of said mitral and tricuspid valves. But it can also be used with other valves, for example aortic and pulmonary valves.

Another type of known ring is made, for example, with fifteen implantable rigid oval-platforms in sequence, plus two ending suture platforms. Two of these platforms are visible on FIG. 5 of the present application.

Figure 5:
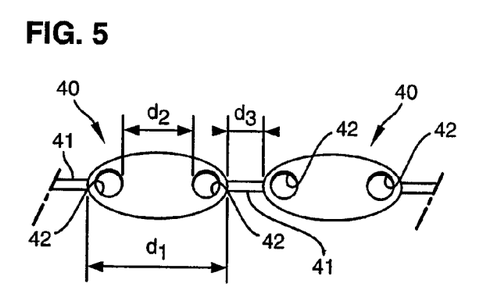
FIG. 5 is a top view of two linked-together suture platforms which form part of an annuloplasty ring.

The length $d_1$ of each platform 40 is 5.5 mm±1 mm, with two suture holes 42, approximately 3.0 mm apart ($d_2$) in sequence.

They are linked by a joint 41, whose length $d_3$ is approximately 2 mm.

Such platforms 40 and joints 41 are integral and preferably injection-molded from polyester, including 20% of barium sulphate for radio-opacity.

Figure 6:
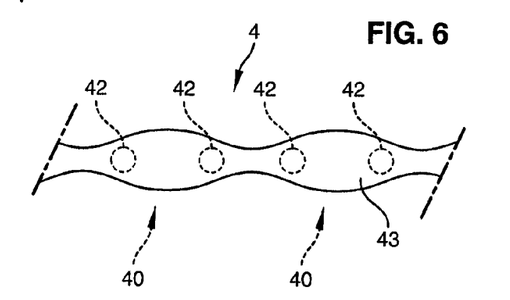
FIG. 6 is similar to FIG. 4, the platforms being covered by a coating.

As can be seen in FIG. 6 of this application, polyester thread 43 is braided over the platforms 40, leaving flexible joints 41 between said platforms. The joints are heat-sealed to prevent fraying of the polyester thread when unused suture-platforms are cut away.

Because the rigidity of the ring 4 is segmental and not continuous, with intervening segmental flexibility at the joints 41, the ring is able to maintain its normal three-dimensional shape. The rigidity of the suture-platforms 40 also guarantees either a measured plication or stabilization of annular tissue beneath the suture-platform with a mattress suture.

The rigid suture-platforms 40 categorically prevent any crimping or foreshortening of the longitudinal dimension of the ring 4, since each suture incorporates a single separate non-deformable rigid element (i.e. a platform 40), guaranteeing precision of the final implant dimension. Since the polyester braiding has almost no elasticity, the ring 4 also guarantees a fixed maximum circumference, preventing late annular dilatation in whatever portion of the annulus the ring is attached.

The overall 7.5 mm. interval spacing of the suture-platforms 40 guarantees secure apposition of the ring 4 to the tissue annulus, since nearly 75% of the circumferential length of the annuloplasty ring 4 consists of the sum total of all the suture-platforms 40, each of which engages the tissue annulus by an individual mattress suture.

The implantable length of the ring is 112.5 mm, long enough to accommodate valves of any size, even if complete circumferential coverage of the annulus is required.

The heat-sealed joints 41 create overall flexibility and allow the ring 4 to be customized to any size to cover any percentage circumference of the mitral or tricuspid annulus, by simply cutting away the unwanted suture-platforms 40.

Flexible joints 41 also reduce overall tension on each of the individual sutures by reducing any shared tension from other sutures, which would be the case with any rigid ring possessing continuous rigidity and forcing the annulus into a prescribed shape.

Nevertheless, because of the flexibility of the ring, a great dexterity is needed to implant it, without any help.

So there exists a need for a support for this type of ring which could help the surgeon for its implantation in an annuloplasty surgery.

Another need exists for a support than can be used whatever the final number of platforms which will be implanted.

SUMMARY OF THE INVENTION

In order to meet the above and other needs, the present invention provides an upper face, a lower face, and a closed peripheral edge with means for accommodating and supporting said suture platforms of said annuloplasty ring.

According to other additional but not limiting features of this holder:

said means for accommodating and supporting said suture platforms include recesses made in said peripheral edge, each recess being intended to accommodate a platform; said means for accommodating and supporting said suture platforms also include support legs which project outwardly from and parallel to said lower face;

said legs comprise a through hole for receiving a needle of suture;

two support legs are associated which each recess;

said means for accommodating and supporting said suture platforms also include locking legs which project outwardly from and parallel to said upper face;

said means for accommodating and supporting said suture platforms also include:

support legs which project outwardly from and parallel to said lower face;

locking legs which project outwardly from and parallel to said upper face; and wherein two support legs and one locking leg are associated which each recess;

said locking leg extends between said support legs;

the holder comprises a cutting guide groove between two adjacent recesses;

said upper face comprises a mark identifying the location of the recess intended to accommodate the middle platform of said ring;

the holder comprises attaching means for attaching opposite end platforms of said ring;

said attaching means comprise at least a through hole;

said upper face comprises a set of numeral marks which correspond to the numbers of platforms to be sutured;

said numeral marks are disposed symmetrically with respect to said "middle" mark;

at least a part of numeral marks are indicated under the form "n−1/n" on a first side of said "middle" mark and "n/n+1" on the second side of said "middle", n being the total number of platforms of the ring to be implanted;

it comprises a central hole for receiving a removable hand grip;

said upper face is flat;

the holder is transparent, or at least translucent;

it has a shape suitable for implanting an annuloplasty ring either on the annulus of a mitral valve or on the annulus of a tricuspid valve;

it has an axis of symmetry, and its border includes a part generally perpendicular to said axis and two joined curved convex parts of increasing radius.

Other important aspects of the invention will become apparent from the following detailed description of preferred embodiments.

BRIEF DESCRIPTION OF THE DRAWINGS

Preferred embodiments of the invention will be described with respect to the accompanying figures in which.

DETAILED DESCRIPTION OF PREFERRED EMBODIMENTS

In reference to FIG. 1 to 4 is shown a holder 1 according to the invention.

This holder has a general shape which is similar to the shape of an annulus of a mitral or tricuspid valve which must be repaired.

It is manufactured from a rigid and biocompatible material, for example from polycarbonate. The holder 1 is preferably transparent or at least translucent, in order to permit to see through.

Said holder 1 comprises an upper face 10, a lower face 11 and a closed peripheral edge 2.

Figure 1:
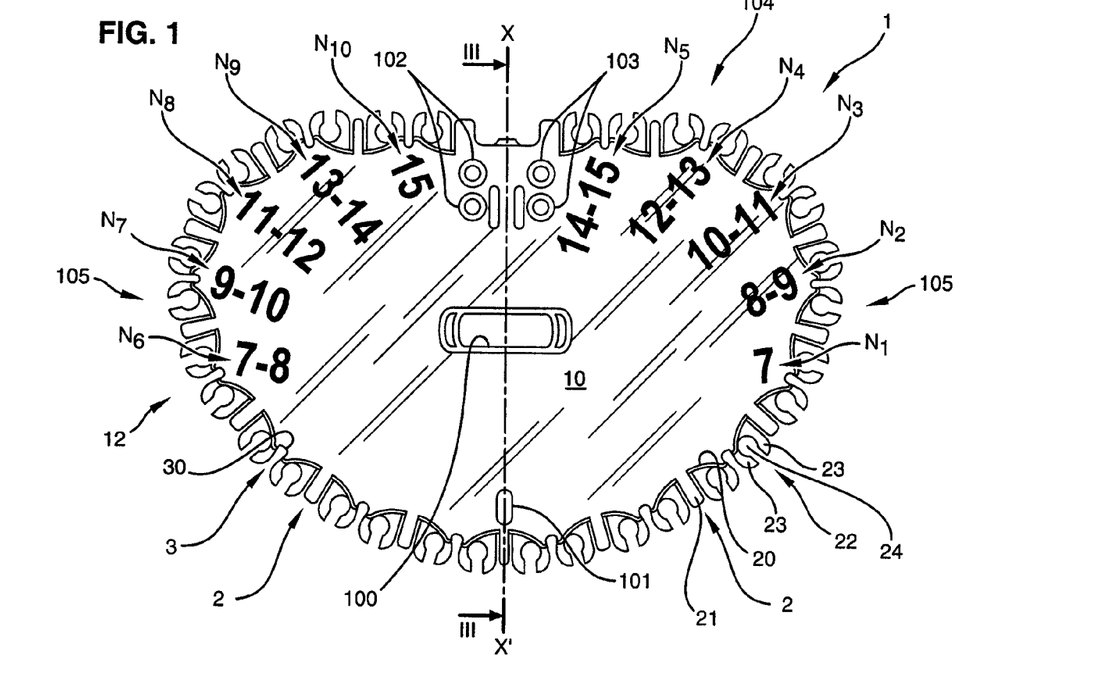
FIG. 1 is a top view of a holder for an annuloplasty ring according to an embodiment of the invention.
Figure 2:
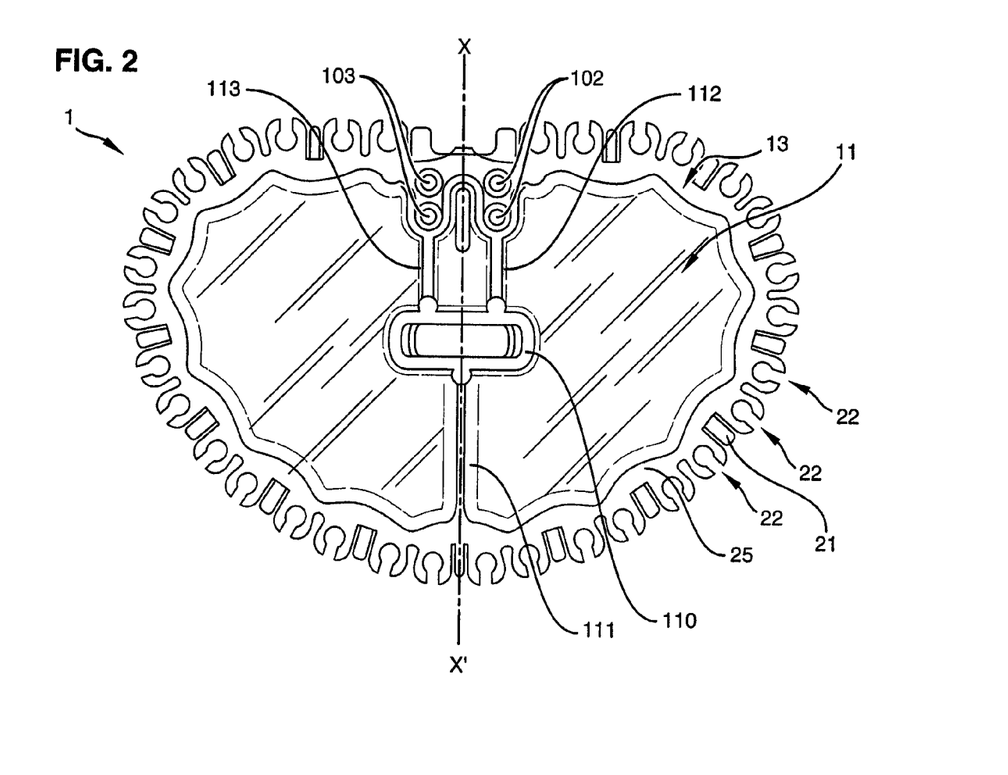
FIG. 2 is a rear view of the holder of FIG. 1.

Axis X-X' of FIGS. 1 and 2 is a longitudinal axis of symmetry. In other words, part of the holder which is on the left side of axis X-X' is the image of the right part.

Said shape is approximately between an oval and a circle. More precisely, it comprises a border which includes a part 104 generally perpendicular to said axis X-X' and two joined curved convex parts 105 of increasing radius.

Upper face 10 is advantageously flat, in order not to retain corporal liquids when the holder is used in the body of a patient.

Figure 3:
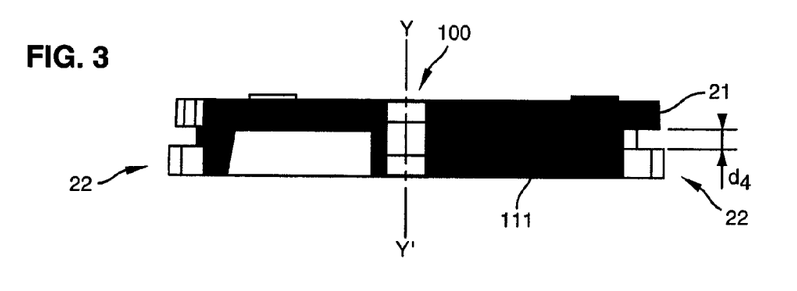
FIG. 3 is a cross-sectional view along line III-III of FIG. 1.
Figure 4:
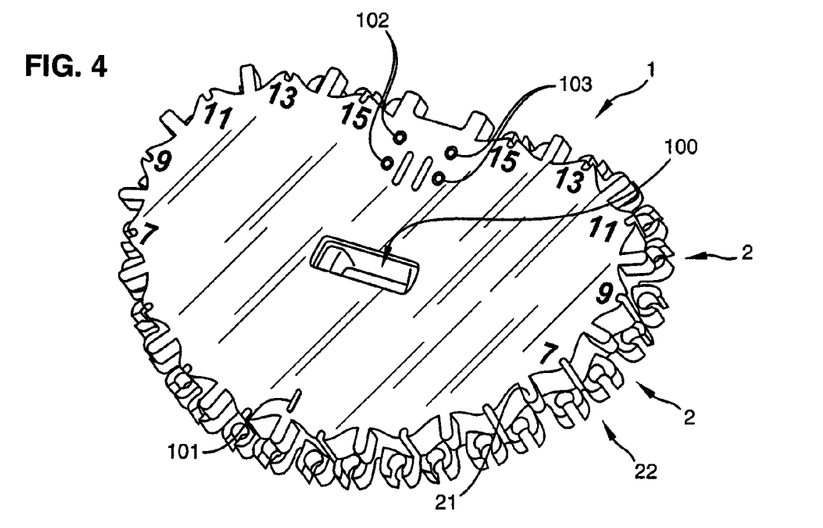
FIG. 4 is a tridimensional view of the holder of FIG. 1.

Lower face 11 is also flat, but is surrounded by a peripheral skirt 25 of significant thickness. Three parallel ribs 111, 112 and 113 extend longitudinally from skirt 25 to a closed wall 110 which surrounds a transversal and centered opening 100.

Peripheral skirt 25, ribs 111, 112 and 113 have the same thickness.

Opening 100 serves to accommodate a removable handle or hand grip, as will be seen thereafter.

According to an important feature of the invention, the peripheral edge 2 comprises means for accommodating and supporting suture platforms 40 of an annuloplasty ring such as the ring 4 of FIGS. 5 and 6.

In a preferred embodiment of the invention, said means for accommodating and supporting include recesses 20 made in said peripheral edge 2.

In the example of FIG. 1 to 4, the holder 1 includes seventeen recesses 20, each recess being intended to receive a platform of an annuloplasty ring.

These recesses 20 have a shape similar to a half of an oval, i.e. a shape which fits with a longitudinal edge of a platform 40 of ring 4.

According to another feature of the invention, said means for accommodating and supporting said suture platforms include support legs 22 which project outwardly from and parallel to lower face 11.

More precisely, said legs 22 extend from said skirt 25.

In the example of FIG. 1 to 4, there are two legs 22 per recess 20. When seen from above (as in FIG. 1), said legs extend between the opposite ends of the corresponding recess 20.

Each leg 22 is "open". By the term "open", it is understood that there exists a hole or opening 24 in the leg 22. This opening 24 not only goes through the thickness of the leg 22, but also extends outwards. Consequently, the opening 24 separate the leg 22 in two branches 23.

As it will be seen hereafter, the opening is useful to introduce a needle.

According to another feature of the invention, said means for accommodating and supporting said platforms include locking legs 21 which project outwardly from and parallel to said upper face 10.

When seen from above (as in FIG. 1), one leg 21 extends between the two supporting legs 22 of each recess 20.

And the vertical distance $d_4$ (FIG. 3) between the lower face of a leg 21 and the upper face of a leg 22 is approximately close to the thickness of a platform 40.

Between two adjacent recesses 20 extends a cutting guide groove 3, whose terminal end 30 extends approximately in the direction of the center of the holder 1.

Said upper face 10 comprises a mark 101 identifying the location of the recess 20 intended to accommodate the middle platform 40 of ring 4. In the example of the accompanying figures, said mark take the shape of a short line. But other types of marks are possible, for example, the term "middle", or a symbol like a triangle. This mark is aligned with said longitudinal axis X-X'.

Opposite to said mark 101, on the other side of the holder 1, there are two parts of traversing holes 103 intended to receive sutures for attachment of the terminal platforms of the ring 4 to the holder 1.

According to a feature of the invention, the upper face 10 comprises a set of numeral marks $N_1$ to $N_{10}$, in the vicinity of some of the recesses 20, which correspond to the numbers of platforms to be sutured. In FIG. 1, a great part of the numeral marks are indicated under the form "n–1/n" or a first side of said mark 101 and "n/n+1" on the second side of said mark 101. The number "n" is the total number of platforms 40 of the ring to be implanted.

Placement and use of holder 1 on a mitral valve will now be described, especially with reference to FIG. 7 to 18.

Figure 7:
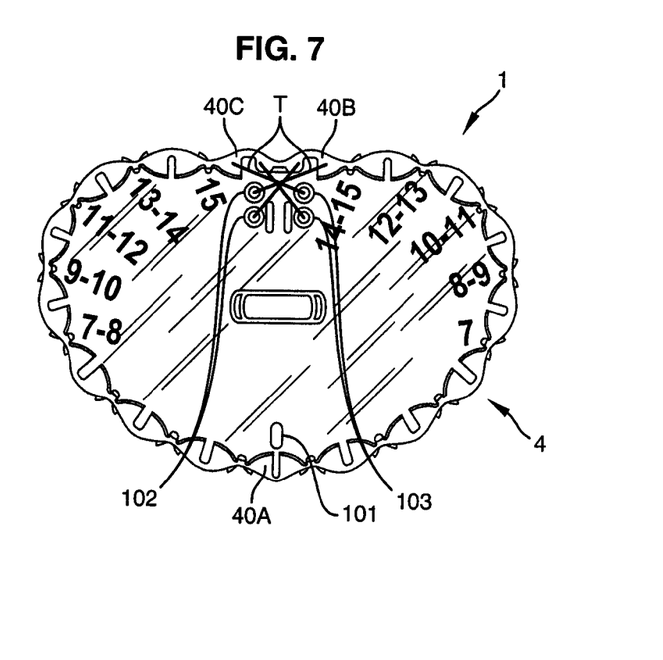
FIG. 7 is a front view of the holder of FIG. 1, with an annuloplasty ring attached to it.

Firstly, a ring 4 is attached to the holder, as shown on FIG. 7. Middle platform 40A is introduced in the recess 20 which is in front of mark 101. The same applies for each platform 40.

Consequently, said platforms 40 fit with corresponding recesses 20. They are supported by legs 22 and locked in position by legs 21. Recesses 20, legs 22 and their openings 24 are sized in order to have platforms' openings 42 aligned with holder's openings 24.

Finally, end platforms 40B and 40C are linked to the holder 1 by introducing threads T in their openings 42, and attaching them to holes 102 and 103 of the holder.

Figure 8:
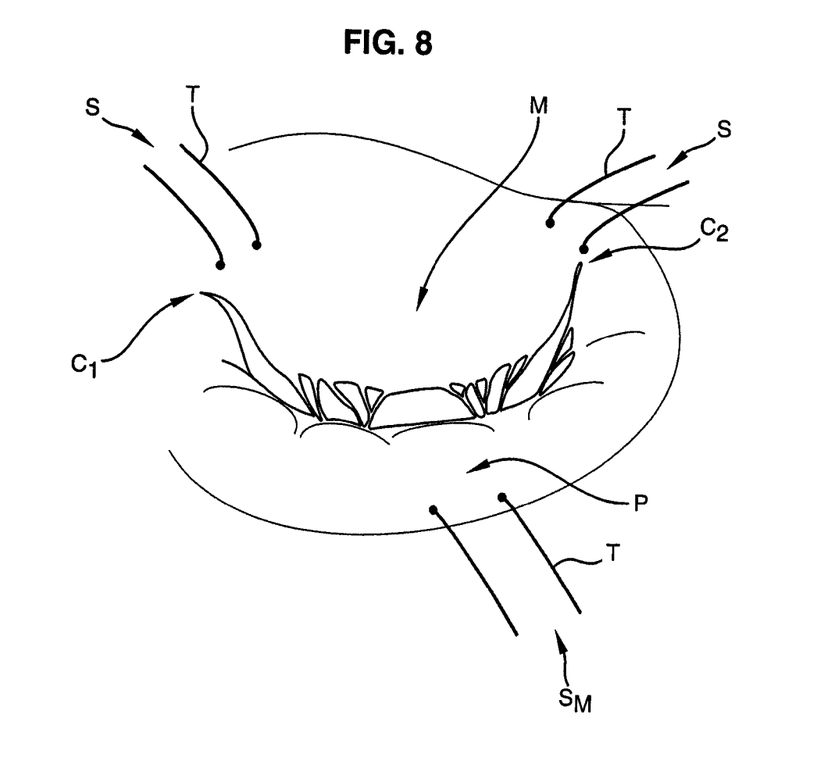
FIG. 8 is a perspective view of a mitral valve which has to be equipped with an annuloplasty ring.

Referring to FIG. 8, which is a perspective view of a mitral valve which has to be repaired, the surgeon usually places one suture S (made of a thread T) at each commissure $C_1$, $C_2$, uses a lateral traction to straighten the anterior annulus and places one "middle" suture $S_M$ in the center of the posterior annulus P.

It is possible to place additional sutures in the annulus if necessary, in order to visualize the unfurled anterior mitral leaflet.

In order to achieve a valve orifice with a normal three-dimensional shape and size, and a normal relationship of valve tissue to final annulus dimensions, correct sizing is important.

For mitral and tricuspid annuloplasty in degenerative and rheumatic cases, the surface area of the anterior leaflet is assumed to represent the correct dimension of the normal valve orifice during systole. Accordingly, the anterior leaflet is unfurled and a sizer is applied to the leaflet. The sizer which best approximates the surface area of the leaflet is then chosen. Undersizing is appropriate in cardiomyopathic and ischemic cases unless.

Figure 9:
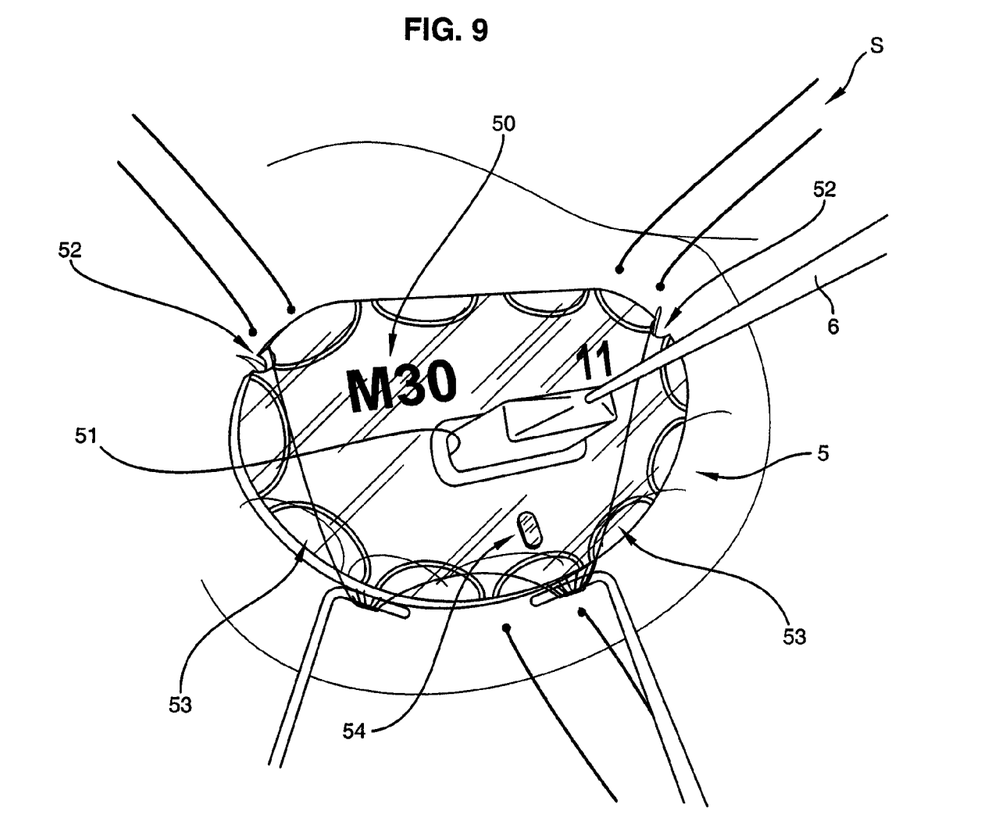
FIG. 9 is a view showing placement of a sizer according to the invention intended to determine the number of suture platforms of the annuloplasty ring to be implanted.

An example of such a sizer is visible on FIG. 9. This sizer 5 is a part of set of different sizers (for example nine sizers).

It is made, for example, of polycarbonate and has a shape corresponding to the shape of the annulus which has to be repaired. Its upper and lower sides are flat.

The number "30" on the left, in association with the letter "M", constitutes a typical size 50 with which surgeons is usually familiar. It refers to the intercommissural distance in millimeters at either extremity of the anterior mitral leaflet and assumes a normal relationship between the intercommissural distance and the circumference of the valve orifice. The number "11" on the right indicate the number of suture-platforms 40 (and, therefore, the number of individual mattress sutures) corresponding to the given ring size.

The hole 51 in the middle of the sizer 5 is designated to engage a removable handle 6.

Notches 52 are present at the end of the straight side of the sizer 5 to indicate the position of the two commissures $C_1$ and $C_2$ (anterior and posterior) straddling the anterior leaflet side. The surface area of each sizer, therefore, correlates closely in most cases to the distance between the notches.

Additional half-oval markings 53 are present along the perimeter of the sizer to represent the position and number of suture-platforms on the final dimension of the tissue annulus required for a given size. The surgeon could add an extra suture-platform.

A final "middle" mark 54 is present in the middle of the curved portion of the sizer to indicate where the "middle" suture is placed.

It is recommended that sizing be done first, in order to determine the correct number of sutures required.

The number of sutures depends on the size of the ring required, with larger rings requiring more sutures. For complete mitral rings, a total of 9-15 sutures are required. For tricuspid rings, a total of 7-12 sutures are usually required.

Individual braided polyester horizontal mattress sutures S, 2-0 for mitral (CARDIOFLON® or CARDIOXYL®) and either 2-0 or 3-0 for tricuspid (CARDIOFLON® or CARDIOXYL®) are placed in the tissue annulus to correspond one-to-one to the required number of suture-platforms of a given ring size. It is recommended that the needle is introduced 1-2 mm. behind the annulus with the needle always aimed toward the ventricle at a 100 angle, coming back out after traversing the annulus 1-2 mm behind the annulus. Always aiming the needle toward the ventricle will eliminate the risk of injuring the aortic valve, the circumflex coronary artery and the A-V node. Keeping the angle of approach at only 10° will eliminate the risk of engaging leaflet tissue or chordae in the suture. For plicating sutures, a ⅜-curve needle is easier to manipulate without the need to bend the wrist as much as with a ½-curve needle.

It is suggested that the valve M be sized first in order to know how many sutures will be required. Some surgeons prefer placing annular sutures early, in order to aid in exposure. If the valve is sized first, the surgeon will then know exactly how many sutures S to place.

For the mitral valve M, the "middle" horizontal mattress suture can be placed first in sequence in the middle of the posterior annulus. The sizer can then applied to the tissue annulus to indicate the exact position of the "first" and "last" horizontal mattress suture, corresponding to the position of the ends of the annuloplasty ring. If a partial ring is desired, sutures in the intertrigonal portion of the anterior annulus can simply be eliminated. After the "middle" suture and the "first" and "last" sutures are placed, the remaining required horizontal mattress sutures are spaced according to the amount of tissue engaged with each suture in the intervening annulus.

Said sizer 5 is placed over the anterior mitral leaflet with the notches 52 at the commissures $C_1$ and $C_2$.

With the sizer against the anterior annulus, the surgeon places the two intercommissural sutures S in the annulus corresponding to the desired location of the "first" and "last" suture-platforms as indicated by the half-oval markings on the sizer, depending upon how far around the annulus the surgeon chooses to go.

Figure 10:
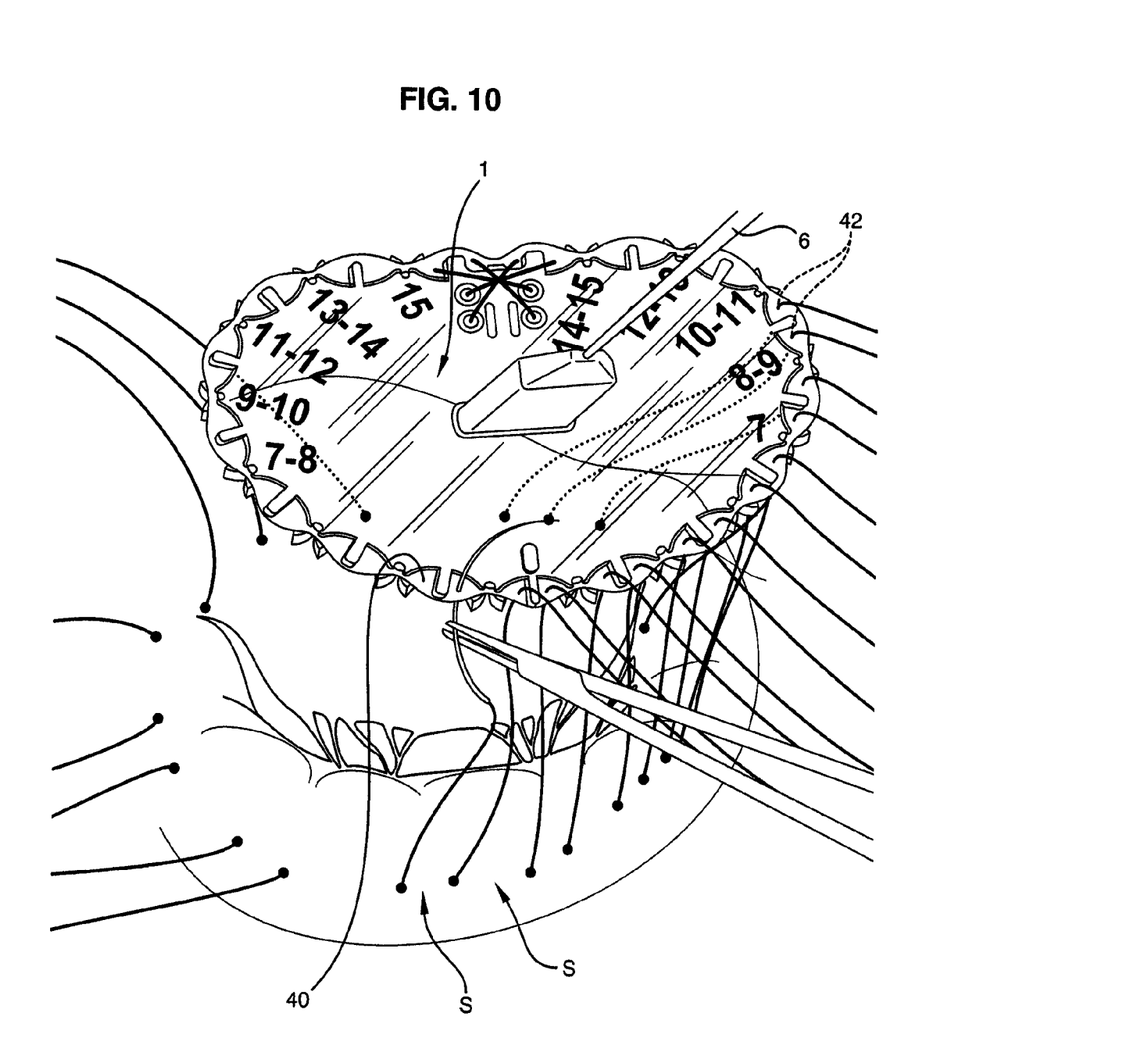
FIG. 10 to FIG. 15 are views showing implantation of the ring on said mitral valve.

Turning now to FIG. 10, the surgeon uses openings 24 as suture guides and places individual mattress sutures S through the suture platforms 40, leaving the ring 4 on the holder 1.

Figure 11:
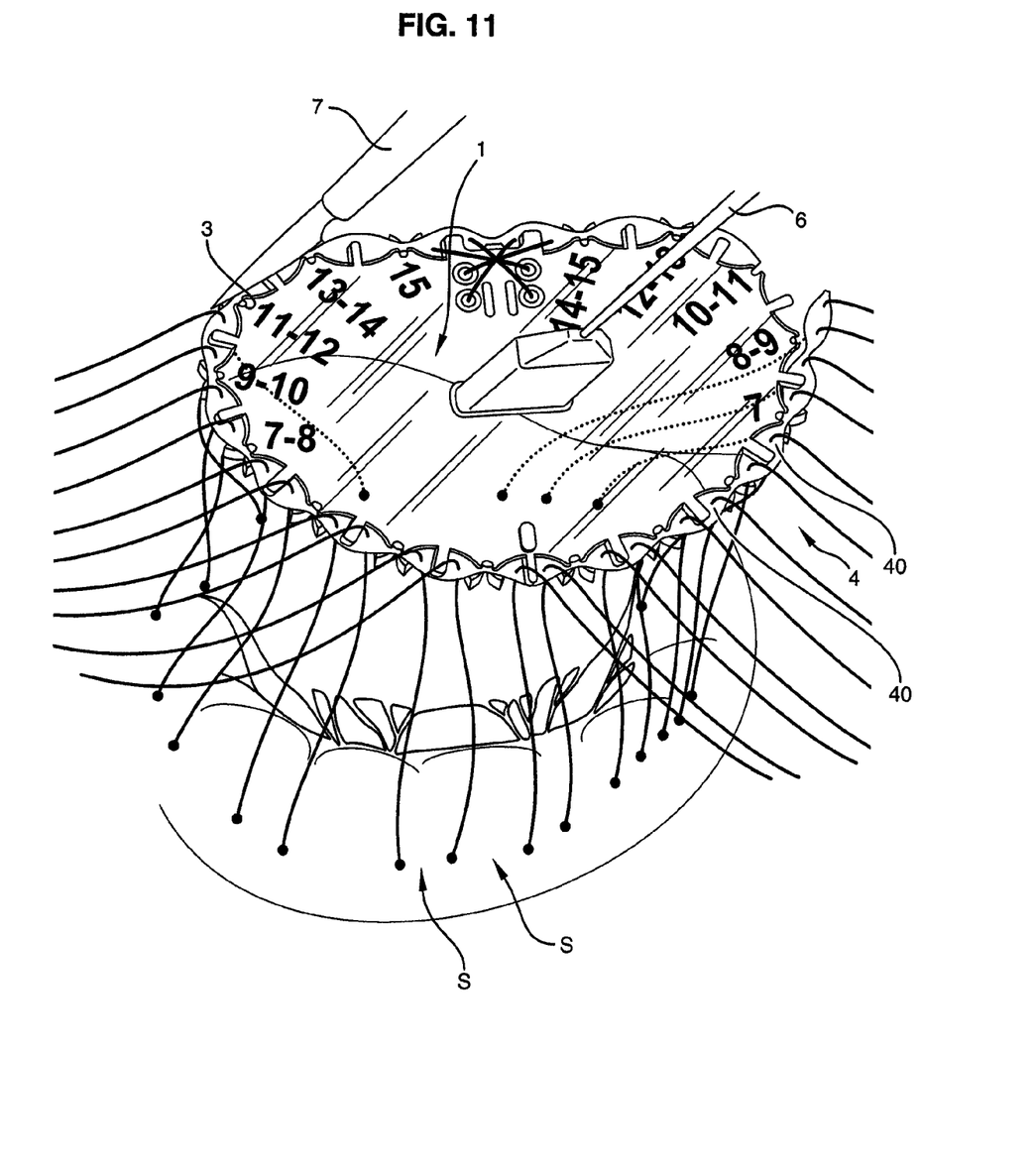

Once all sutures are placed one-to-one in the ring 4, the surgeon cut the ring at the appropriate joints, using a sharp blade 7 in the cutting guide grooves 3 on the outer side of the "first" and "last" suture platform 40 (see FIG. 11). Because he knows that only eleven platforms have to be used, he just has to cut the joints just in front of "10-11" and "11-12", i.e. N3 and N9 marks.

Figure 12:
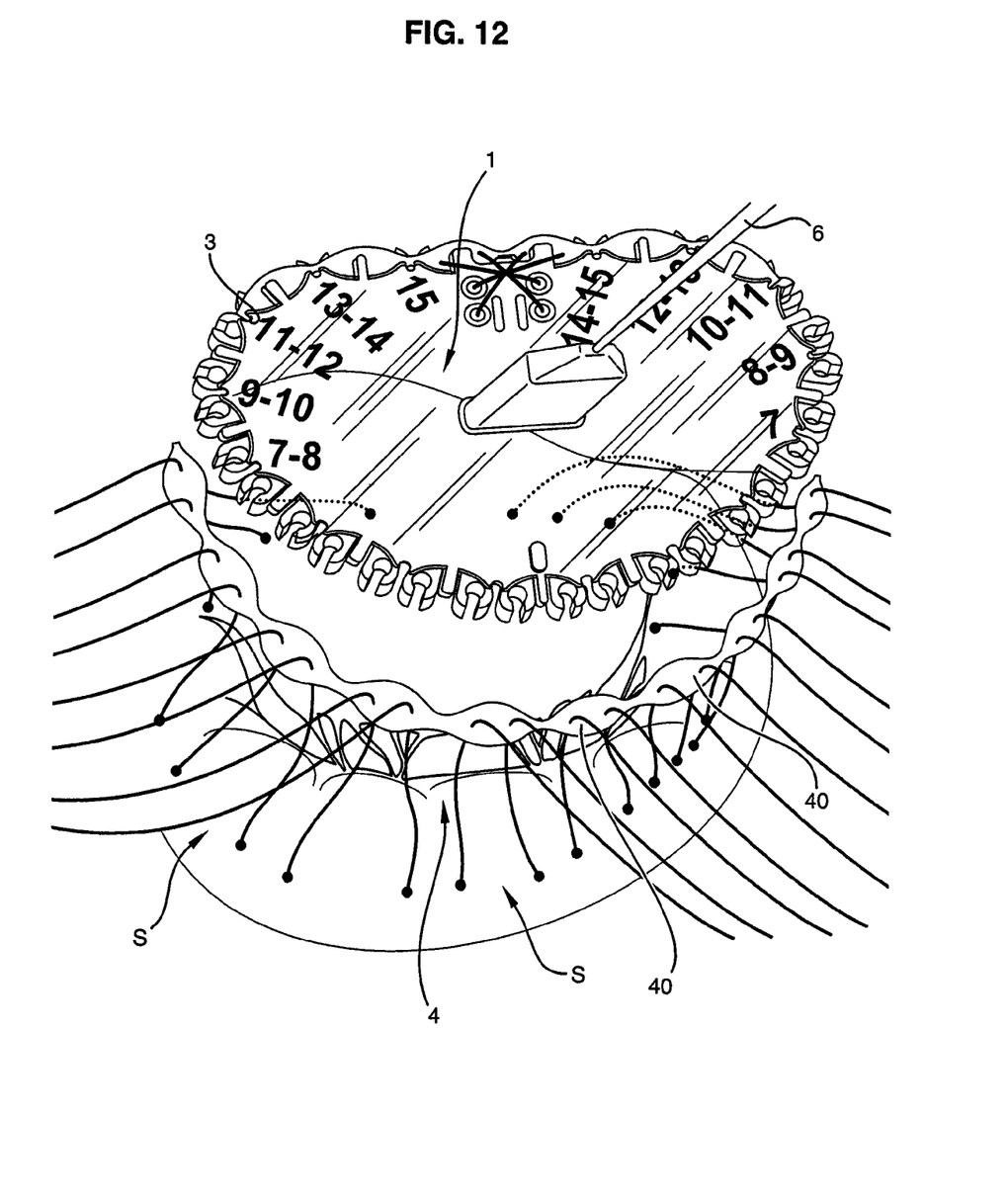

With the ring 4 free from the holder 1, the surgeon slides the ring 4 onto the annulus (FI 12). Unused platforms 40 remain on the holder 1.

Figure 13:
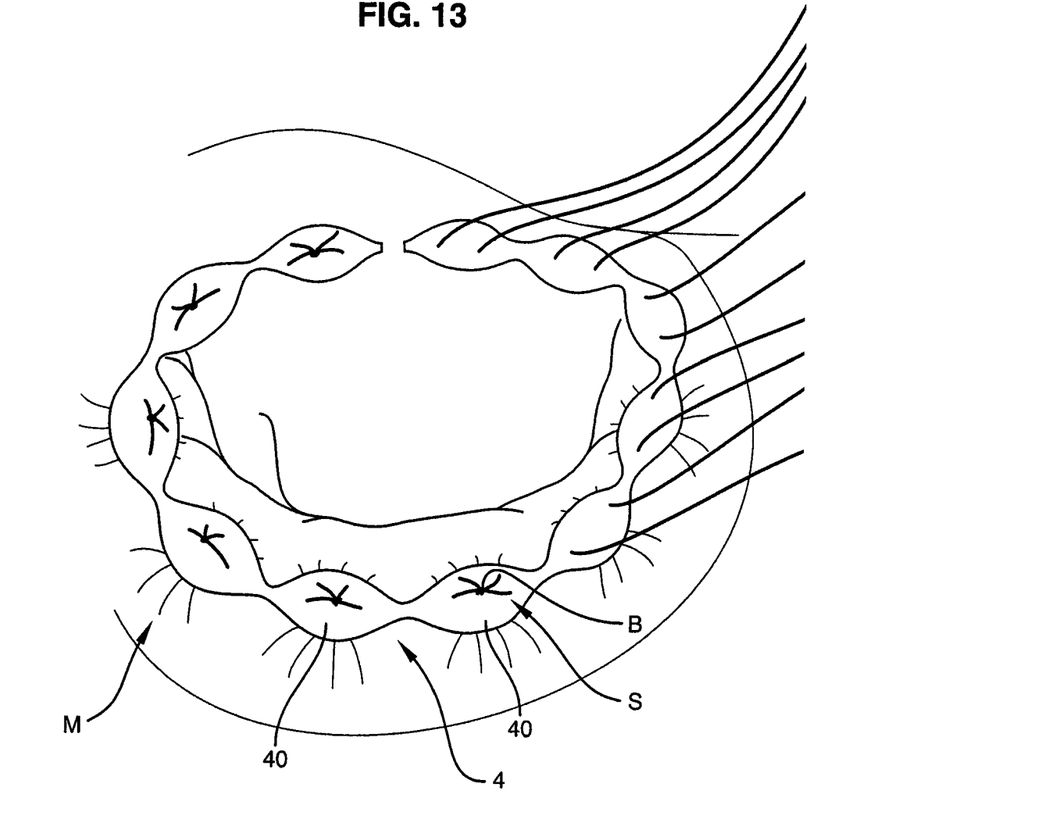

Turning now to FIG. 13, the opposite ends of each suture S are linked together and cut, so as to form a surgeon's knot B.

Figure 14:
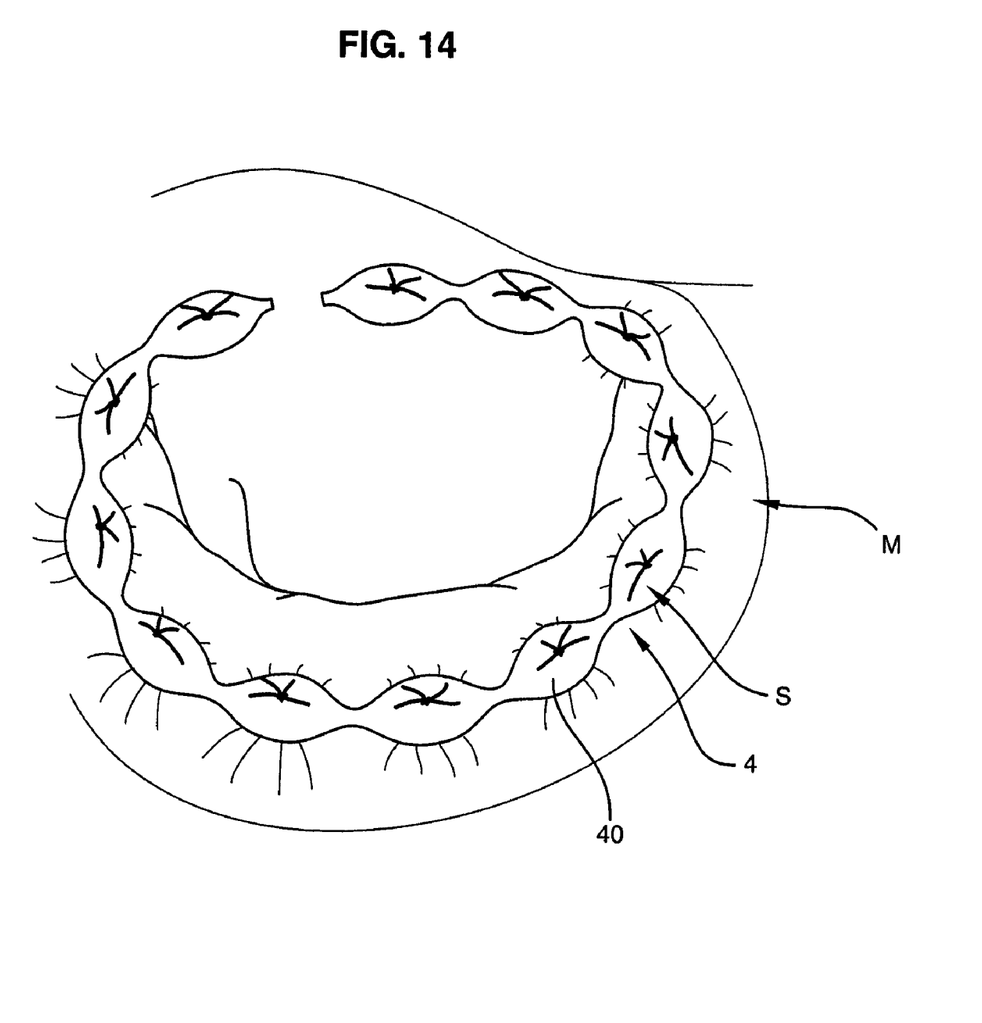
Figure 15:
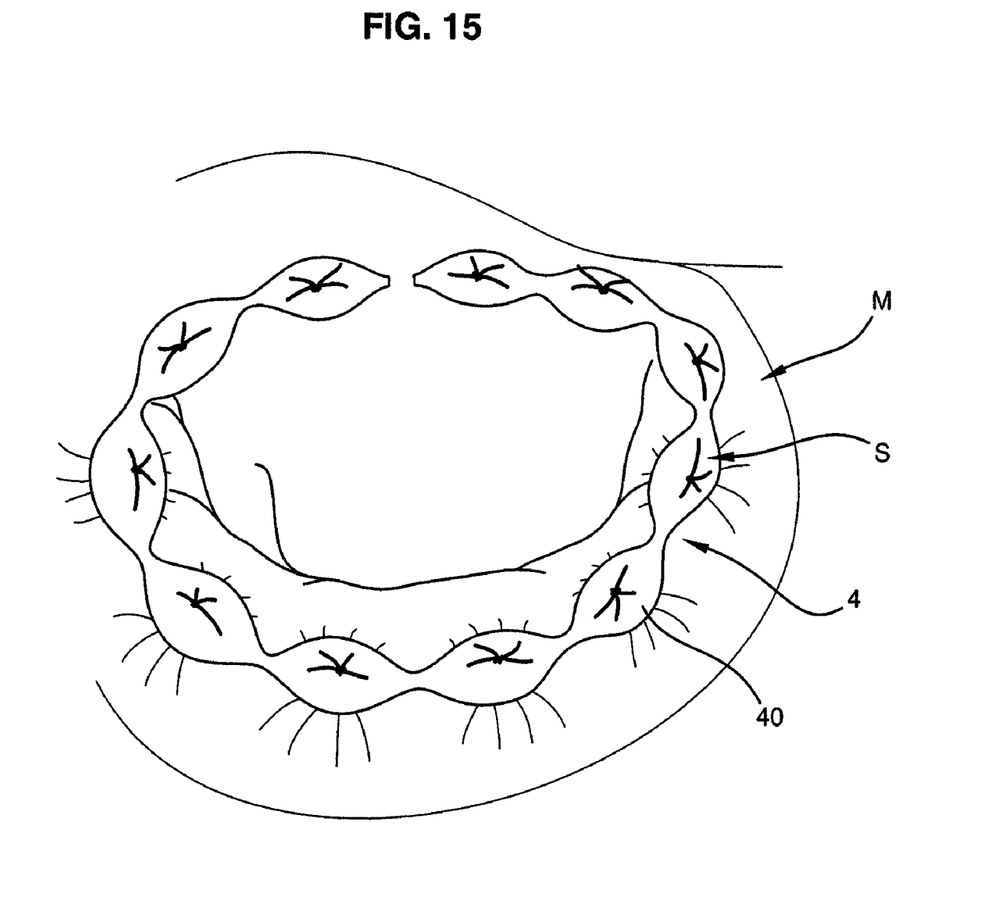

FIGS. 14 and 15 illustrate respectively an open ring 4 and a closed ring 4 placed around a mitral annulus.

For annular stabilization without plication (as is usual in the anterior mitral annulus), the sutures should incorporate exactly 3 mm of tissue, corresponding to the precise distance between the two opening 42 of each suture-platform 40 of the ring 4. For annular plication (as is usual in the posterior mitral and anterior and posterior tricuspid annulus), larger amount of tissue are incorporated within each horizontal mattress suture loop underneath the suture platform 40.

Figure 16:
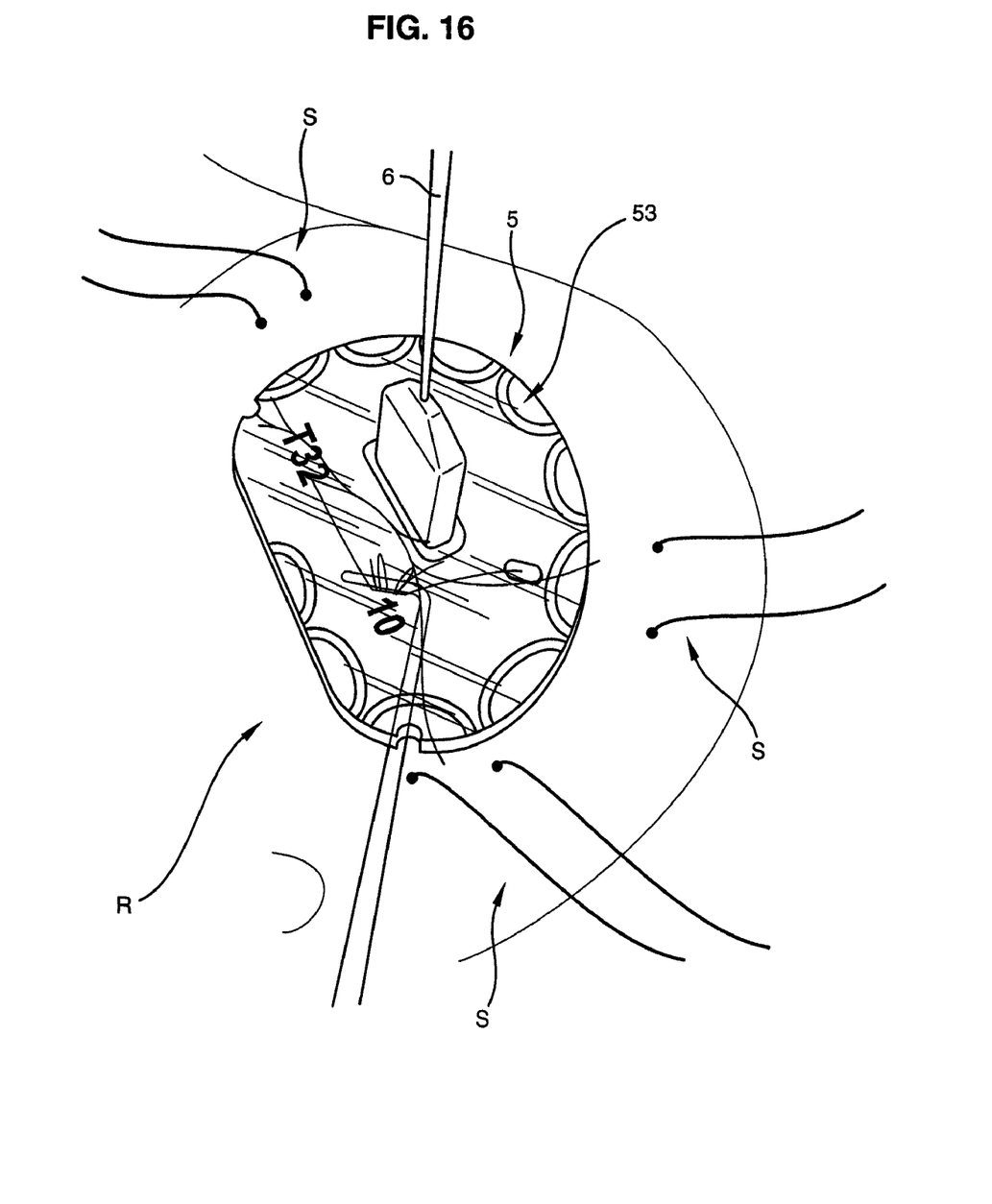
FIG. 16 to FIG. 18 are views showing implantation of an annuloplasty ring on a tricuspid valve.
Figure 17:
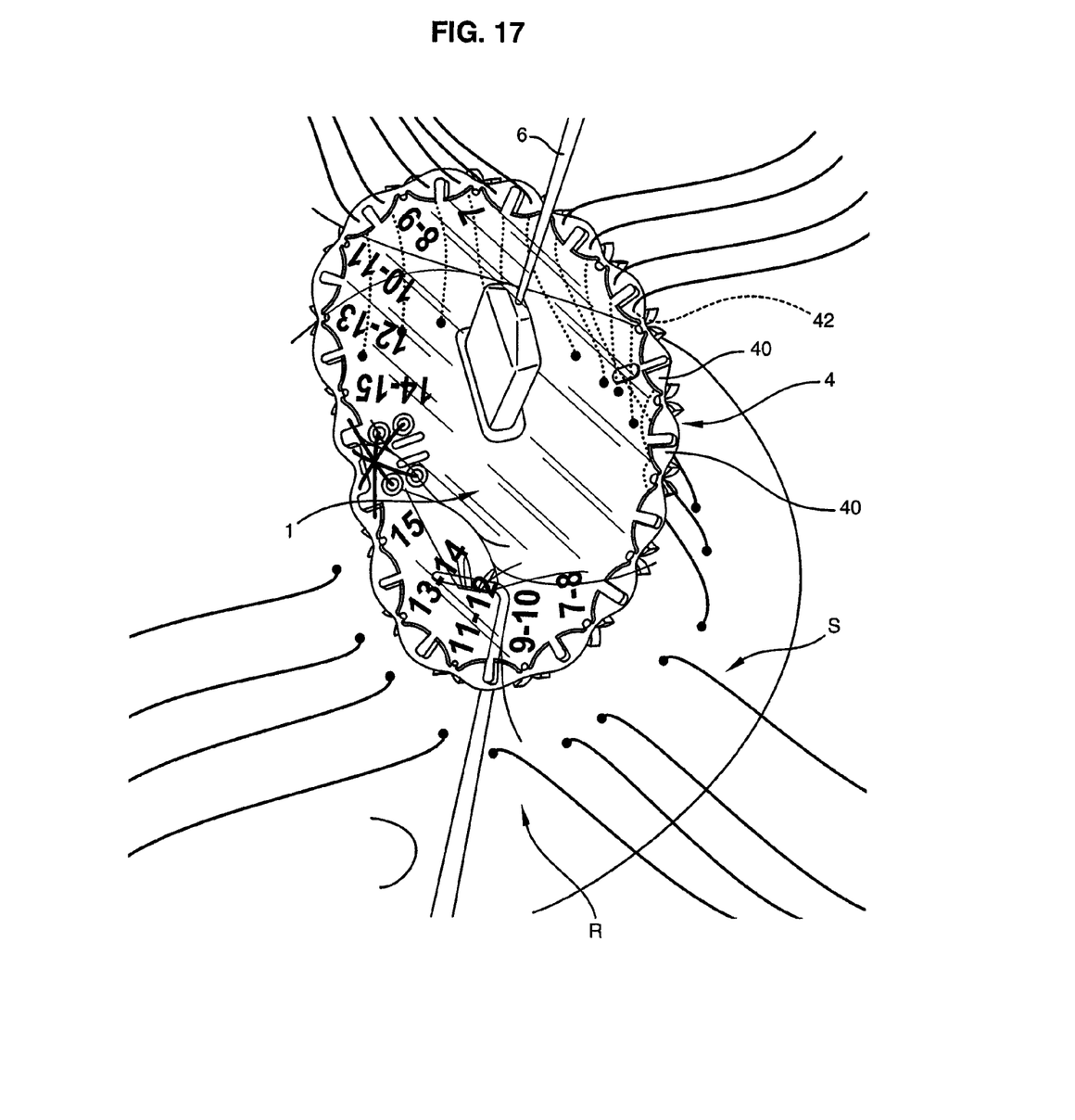
Figure 18:
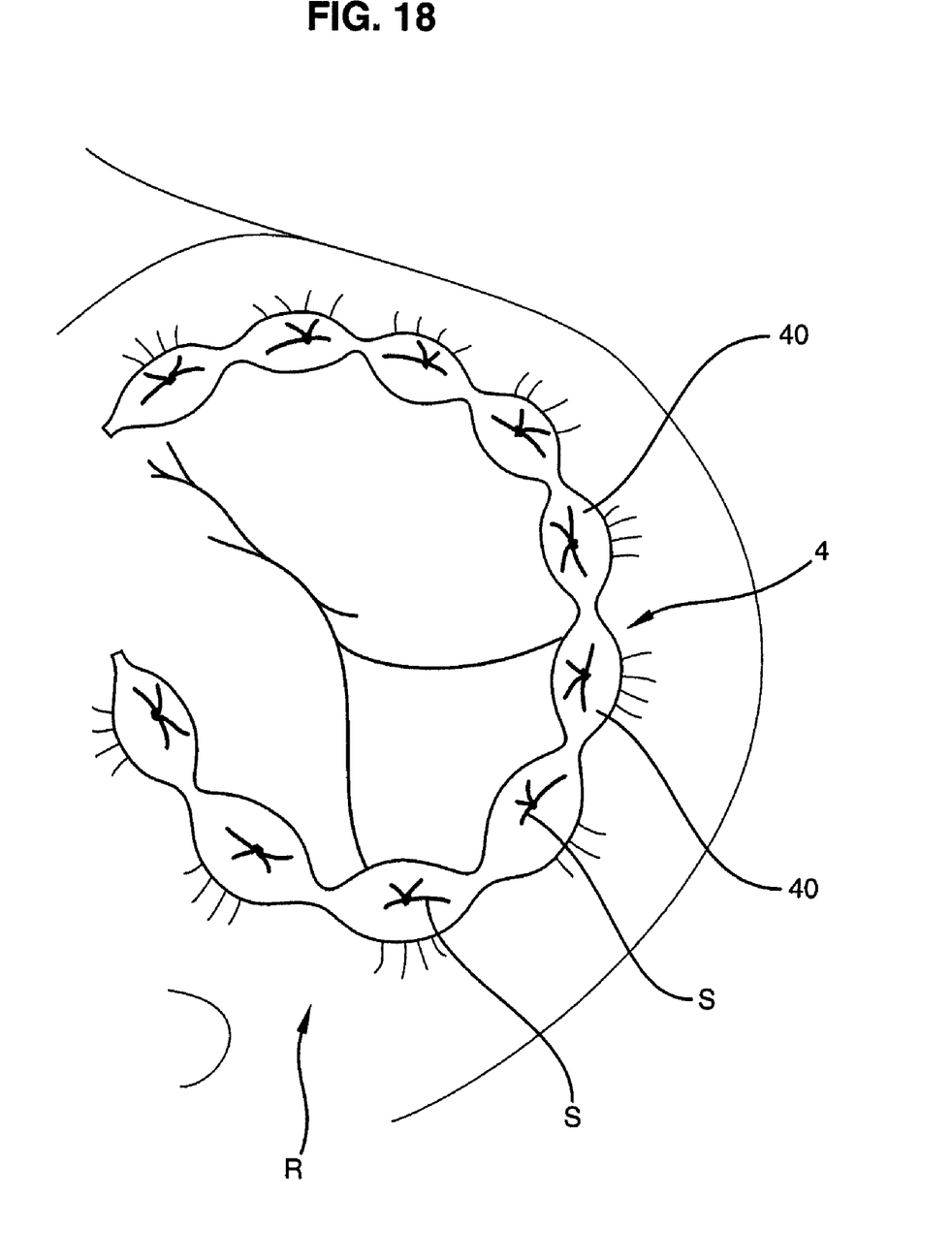

Placement and use of the holder 1 on a tricuspid valve repair will be now described, especially with reference to FIG. 16 to 18.

The sizing of the annulus is made using a sizer 5 quite similar to the sizer 5 of FIG. 9.

This sizer 5 has also half-oval markings 53. But a space without marking is present along the perimeter of the left hand portion of the straight side of the sizer. This represents the area of the conduction system, where suturing is avoided.

In reference to FIG. 17, using the suture guides opening 24 on the holder 1, the surgeon places the individual mattress sutures S through the suture platforms 40, leaving the ring 4 on the holder. The "first" suture should be placed in the vertical part of the anterior annulus, just above the anterior-septal commissure.

Then, the "first" and "last" platforms 40 are cut and the holder is separated from the remaining ring 4.

The surgeon will preferably tie each mattress suture S with seven knots.

The overall 7.5 mm. interval spacing of the suture-platforms guarantees secure apposition of the ring to the tissue annulus, since nearly 75% of the circumferential length of the annuloplasty ring consists of the sum total of all the suture-platforms, each of which engages the tissue annulus by an individual mattress suture. The implantable length is 112.5 mm, long enough to accommodate valves of any size, even if complete circumferential coverage of the annulus is required.

The heat-sealed joints create overall flexibility and allow the ring to be customized to any size to cover any percentage circumference of the mitral or tricuspid annulus, by simply cutting away the unwanted suture-platforms.

Flexible joints should also reduce overall tension on each of the individual sutures by reducing any shared tension from other sutures, which would be the case with any rigid ring possessing continuous rigidity and forcing the annulus into a prescribed shape.

It is important to note that:
sizing should be done carefully and precisely. Oversizing could result in inadequate coaptation of the valve leaflets, leading to residual mitral regurgitation. Undersizing, could result in systolic anterior motion (SAM), left ventricular outflow tract obstruction or mitral stenosis.
removal of unwanted suture-platforms must be done with a surgical blade and must take place in the middle of the heat-sealed joints to avoid exposing the suture-platform. The holder, with the cutting guides, is designed to facilitate this procedure.
removal of the ring from the holder by cutting the two sutures at the top of the holder must not take place. For endoscopic introduction of the ring, it is recommended that sizing and cutting of the ring take place before it is introduced into the endoscope, not after. The holder is designed to retain the unwanted, detached suture-platforms as a unit, in order to avoid loose ring remnants entering the surgical field.

What is claimed is:

1. A holder for an annuloplasty ring of a plurality of suture platforms directly linked-together by integral joints, the suture platforms each having a thickness, said holder comprising;
   an upper face, a lower face, and a closed peripheral edge with means for accommodating and supporting said suture platforms of said annuloplasty ring, said means including recesses made in said peripheral edge, each recess being intended to accommodate a platform, and support legs which project outwardly from and parallel to said lower face and locking legs which project outwardly from and parallel to said upper face,
   wherein the support legs have an upper face spaced a vertical distance from an upper face and a lower face of the locking legs, the spaced vertical distance from said lower face approximately the same as the suture platform thickness.

2. The holder of claim 1, wherein said legs comprise a through hole for receiving a needle of suture.

3. The holder of claim 1, wherein two support legs are associated which each recess.

4. The holder of claim 1, wherein two support legs and one locking leg are associated with each recess.

5. The holder of claim 4, wherein said locking leg extends between said support legs.

6. The holder of claim 1, which comprises a cutting guide groove between two adjacent recesses.

7. The holder of claim 1, wherein said upper face comprises a "middle" mark identifying the location of the recess intended to accommodate the middle platform of said ring.

8. The holder of claim 1, which comprises attaching means for attaching opposite end platforms of said ring.

9. The holder of claim 8, wherein said attaching means comprise at least a through hole.

10. The holder of claim 1, wherein said upper face comprises a set of numeral marks which correspond to the numbers of platforms to be sutured.

11. The holder of claim 7, wherein said upper face comprises a set of numeral marks which correspond to the numbers of platforms to be sutured.

12. The holder of claim 1, which comprises a central hole for receiving a removable hand grip.

13. The holder of claim 1, wherein said upper face is flat.

14. The holder of claim 1, which is transparent or at least translucent.

15. The holder of claim 1, which has a shape suitable for implanting an annuloplasty ring either on the annulus of a mitral valve or on the annulus of a tricuspid valve.

16. The holder of claim 15, which comprises an axis of symmetry, and whose border includes a part generally perpendicular to said axis and two joined curved convex parts of increasing radius.

17. A holder for an annuloplasty ring of a plurality of suture platforms directly linked-together by integral joints, said holder comprising:
an upper face, a lower face, and a closed peripheral edge for accommodating and supporting said suture platforms of said annuloplasty ring, with recesses made in said peripheral edge, each recess being intended to accommodate a platform, support legs which project outwardly from and parallel to said lower face and locking legs which project outwardly from and parallel to said upper face, wherein the support legs have an upper face spaced a vertical distance from an upper face and a lower face of the locking legs.

* * * * *